United States Patent [19]
Horenstein et al.

[11] Patent Number: 6,020,344
[45] Date of Patent: Feb. 1, 2000

[54] ENZYME INHIBITORS AND METHODS OF USE

[75] Inventors: Benjamin A. Horenstein, Gainesville, Fla.; Ian B. Parr, Arlington, Mass.

[73] Assignee: University of Florida, Gainesville, Fla.

[21] Appl. No.: 09/127,361

[22] Filed: Jul. 31, 1998

Related U.S. Application Data

[60] Provisional application No. 60/054,459, Aug. 1, 1997.

[51] Int. Cl.[7] ............... A61K 31/445; C07D 211/36; C07D 211/56; C07D 211/92; C07D 211/30
[52] U.S. Cl. ............... 514/315; 546/242; 546/244; 546/224; 546/225; 546/238
[58] Field of Search ............... 514/315; 546/242, 546/244, 224, 225, 238

[56] References Cited

U.S. PATENT DOCUMENTS

| | | | |
|---|---|---|---|
| 4,145,426 | 3/1979 | Grier et al. | 424/267 |
| 5,137,896 | 8/1992 | Van Daele | 514/327 |

OTHER PUBLICATIONS

Van Daele, Synthesis of cisapride, CA 105:183409u, 1986.

*Primary Examiner*—Alan L. Rotman
*Assistant Examiner*—Rita Desai
*Attorney, Agent, or Firm*—Saliwanchik, Lloyd & Saliwanchik

[57] ABSTRACT

Novel enzyme-inhibitory compounds are disclosed. The subject invention further pertains to methods and compositions for the inhibition of bacteria, viruses, parasites, and other pathogens.

13 Claims, 5 Drawing Sheets

FIG. 6

ENZYME INHIBITORS AND METHODS OF USE

CROSS-REFERENCE TO RELATED APPLICATION

This application claims priority from provisional application U.S. Ser. No. 60/054,459, filed Aug. 1, 1997.

The subject invention was made with government support under a research project supported by National Science Foundation (CAREER award MCB-9501866). The government has certain rights in this invention.

BACKGROUND OF THE INVENTION

Despite the existence of many useful antibiotics, bacterial, parasitic, and viral infections remain a major problem affecting human and animal health, agriculture, and industrial processes. The continued emergence of resistant bacteria and viruses heightens the need for the identification of new and effective agents for the inhibition of these pathogens. The most advantageous antiviral and antibacterial agents are those which can be used to selectively control pathogens without posing any health hazards for humans or animals. The identification of such agents is fraught with difficulties and uncertainties due to the biochemical complexities of viral and bacterial pathogens as well as the ability of these organisms to develop resistance. The identification of antiviral and antibacterial agents remains an empirical process requiring extensive effort and the investment of substantial resources.

A particularly serious pathogen to humans is the influenza virus. Influenza virus epidemics occur every winter, causing significant morbidity and mortality in the U.S. population. The disease has a high infection rate and annual costs to the U.S. are estimated to exceed one billion dollars. The elderly are at high risk for serious complications from influenza, and excess mortality in the U.S. is estimated to be 10,000–20,000 each year. Currently available vaccines and drugs have failed to effectively control influenza in humans. Furthermore, vaccines must be reformulated each year in response to antigenic variation and are frequently ineffective against new influenza variants. A need exists for new, broad-spectrum anti-influenza drugs that act by different mechanisms.

Influenza viruses are enveloped RNA viruses that are classified into three serological types: A, B, and C. The two major surface glycoproteins of influenza viruses are hemagglutinin (HA) and neuraminidase (NA). These glycoproteins are essential for infectivity and offer potential targets for antiviral drug development. HA is responsible for viral attachment to host cells by binding to terminal sialic acid residues on host cell surface glycoconjugates, and HA is also involved in mediating membrane fusion. NA (also called sialidase or acy-ineuraminylhydrolase) destroys the host cell viral receptor by catalyzing the hydrolysis of α-2,6-glycosidic bonds to terminal sialic acid residues of surface glycoconjugates. This facilitates release and prevents aggregation of progeny virus. Influenza NA, which accounts for 5–10% of the virus protein, has an approximate molecular weight (MW) of 250,000 and lies mostly outside of the viral membrane.

Sialic acids (N-acetyl neuraminic acid, referred to herein as NeuAc) are nine carbon ketoses which have the unusual feature of a highly acidic carboxyl group ($pK_a$~2.8) immediately adjacent to the anomeric carbon. Sialic acids are typically found in terminal glycosidic linkages of cell surface glycoproteins and glycolipids. A variety of biological phenomena are associated with recognition of sialosides, including viral replication, escape of immune detection, and cell adhesion (Schauer, R. *Trends Biochem. Sci.* 1985, 10, 357–360; *Biology of the Sialic Acids* ed. A. Rosenberg, Plenum Press, New York, 1995) providing considerable interest in the development of inhibitors of sialyltransferases and sialidases for mechanistic and clinical applications (Taylor, G. *Curr. Opin. Struc. Biol.* 1996, 6, 830–837; Colman, P. M., *Pure Appl. Chem.* 1995, 67, 1683–1688; Bamford, M. J. *J Enz. Inhib.* 1995, 10, 1–16; Khan, S. H. & Matta, K. L. *In Glycoconjugates, Composition, Structure, and Function.* pp361–378. ed., Allen, H. J. & Kisailus, E. C. Marcel Dekker, Inc. New York, 1992).

A number of compounds have been evaluated as in vitro inhibitors of influenza neuraminidase, and among the most potent thus far described is 2-deoxy- 2,3-dehydro-N-acetylneuraminic acid (DANA). A DANA analog, 2-deoxy-2,3-dehydro-N-(trifluoroacetyl) neuraminic acid (FANA), exhibited greater in vitro activity (Palese, P., R. W. Compans [1976]*J. Gen. Virology* 33:159–163). Several new DANA analogs have been described that possess in vivo antiviral effects (Von Itzstein, LM et al. [1991] WO 91/16320; O'Neill, G. [1993]*J. NIH Res.* 5:40–42).

The observation that DANA was an effective in vitro inhibitor of NA has resulted in the preparation of a large number of synthetic derivatives varied mainly at the 2-, 4-, 5-, and 6-positions (for example, Meindl, P., G. Bodo, P. Palese, J. Schulman, H. Tuppy [1974] *Virology* 58:457–463; Schreiner, E., E. Zbiral, R. G. Kleineidam, R. Schauer [1991] *Liebigs Ann. Chem.* 129–134; Kumar, W., S. Tanenbaum, M. Brashner [1982] *Carbohyd. Res.* 103:281–285; Vasella, A., R. Wyler [1991] *Helv. Chim. Acta* 74:451–463). Numerous synthetic sialic acid (NANA) analogs (for example, Glanzer, B. I., Z. Gyorgydeak, B. Bernet, A. Vasella [1991] *Helv. Chim. Acta* 74:343–368; Yamamoto, Y., H. Kumazawa, K. Inami, T. Teshimi, T. Shiba [1992] *Tet. Lett.* 33:5791–5794; Mack, H., R. Brossmer [1992] *Tet. Lett.* 33:1867–1870) have also been reported. A few NA inhibitors that are not pyrans or furans have been described, including isoquinolines(Brammer, K. W., C. R. McDonald, M. S. Tute [1968] *Nature* 219:515–517), α-mercaptocinnamic acids and imidazoles (Haskell, T. H., F. E. Peterson, D. Watson, N. R. Plessas, T. Culbertson [1970] *J. Med. Chem.* 13:697–704), oxamic acids (Brossmer, R., G. Keilich, D. Zeigler [1977] *Hoppe-Seyler 's Z. Physiol. Chem.* 358:391–396), the piperidine, siastatin B, and derivatives(Kudo, T., Y. Nishimura, S. Kondo, T. Takeuchi [1993] *J. Antibiot.* 46:300–309), and plant flavonoids (Nagal, T., Y. Miyaichi, T. Tomimori, Y. Suzuki, H. Yamada [1992]*Antiviral Res.* 19:207–217). One attempt at rational design of inhibitors has resulted in a class of compounds based on 2-deoxy-2,3-didehydro-D-N-acetylneuraminic acid (Neu5Ac2en) (Brammer et al., supra).

There remains a need to identify effective compounds which can combat bacterial, parasitic, and viral infections. The ability to use such compounds for other applications such as to modulate immune responses, regulate inflammation, and/or inhibit metastasis would additionally be advantageous.

BRIEF SUMMARY OF THE INVENTION

The subject invention pertains to novel compounds and the use of these compounds to inhibit enzymes which catalyze the glycosyltransfer of N-acetylneuramic acid. Specifically exemplified herein are piperidine compounds which inhibit the enzymatic activity of neuraminidase. In a specific embodiment, the subject invention pertains to compounds which inhibit bacteria, viruses, and/or parasites through the inhibition of neuraminidase.

Other advantageous uses of the unique compounds of the subject invention are described herein. Specifically, in addition to the use of the subject compounds to prevent viral, bacterial, or parasitic infection, these compounds can also be used for immune system modulation, regulation of inflammatory responses, and regulation of cell-cell interactions which are involved in, for example, metastasis.

As exemplified herein, the compounds of the subject invention can be used to inhibit the enzymatic activity of neuraminidases. Neuraminidases, which cleave glycosidic bonds to N-acetylneuraminic acid in glycoproteins, glycolipids, and oligosaccharides, are critical enzymes in a variety of pathogens, including viruses, parasites, and bacteria. In one embodiment, the subject invention provides novel electronic analogs for the N-acetylneuraminic acid oxocarbenium ion. These analogs are useful as inhibitors of enzymes involved in the glycosyltransfer of N-acetylneuraminic acid. By inhibiting the activity of this enzyme utilizing the compounds of the subject invention, it is possible to inhibit the pathogen.

In specific embodiments, the compounds of the subject invention can be used to inhibit viruses such as the influenza virus and bacterial pathogens such as Salmonella, Vibrio, and Clostridium.

DETAILED DISCLOSURE OF THE INVENTION

The subject invention pertains to materials and methods useful for the inhibition of enzymes involved in the glycosyltransfer of N-acetylneuramic acid. The compounds and methods of the subject invention are particularly useful in the prevention and/or inhibition of infections. Specifically exemplified herein are compositions and methods which are useful for the control of bacterial, viral, and/or parasitic infections. Advantageous modulation of immune system responses and cell-cell interactions can also be achieved with the compounds of the subject invention.

In a preferred embodiment, the compounds of the subject invention exert their inhibitory effects by interfering with the enzymatic activity of neuraminidase. In a specific embodiment, the subject invention provides a series of N-substituted piperidines which effectively inhibit neuraminidase. The subject invention further pertains to salts, solvates, hydrates, derivatives, and analogs of the exemplified compounds, so long as such salts, solvates, hydrates, derivatives, and analogs retain the ability to inhibit the glycosyltransfer of N-acetylneuraminic acid. The present invention also provides compositions for inhibiting enzymatic activity which comprise one or more of the inhibitory compounds of the subject invention.

The subject invention further provides novel methods of making the inhibitors, methods of treatment using the inhibitors, and methods of prophylaxis from viral, bacterial, and parasitic infection.

In yet another embodiment, the present invention provides a method of inhibiting enzymatic activity comprising the step of: administering to a subject a pharmaceutically acceptable amount of a composition comprising effective amounts of a pharmaceutically acceptable carrier and an inhibitor compound of the subject invention.

In yet another embodiment, the present invention provides a method of making a composition for inhibiting enzyme activity comprising the steps of admixing effective amounts of a pharmaceutically acceptable carrier with an inhibitor compound of the subject invention Unique structural features which contribute to the advantageous activity of the compounds of the subject invention include:

1. The placement of a nitrogen atom in the piperidine ring in a position analogous to that of the glycosidic carbon in N-acetylneuraminic acid.
2. The incorporation of functionality at carbon atoms 3, 4, and 5 of the piperidine ring which are homologous to the functionality and position of substituents on the six-membered ring of N-acetylneuraminic acid.

Various compounds fall within the scope of this invention. For example, different groups can be attached to the ring nitrogen, including nitrogen, oxygen, and carbon.

Figure 1:
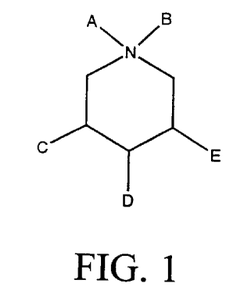
FIG. 1 is a generic structure of certain compounds of the subject invention.
Figure 2:
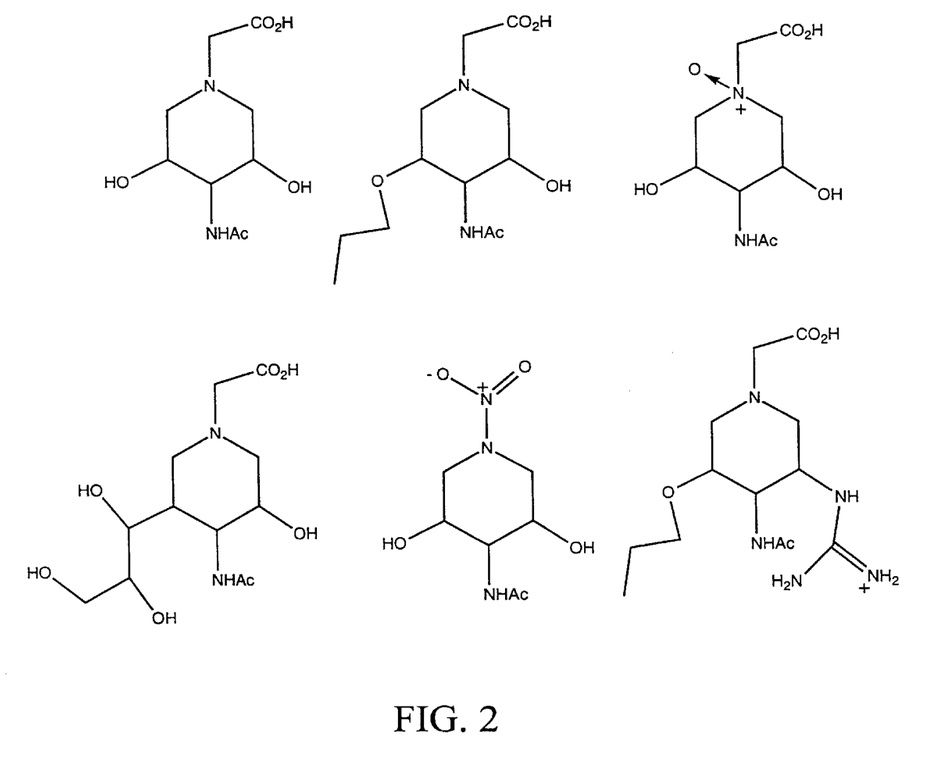
FIG. 2 shows specific compounds of the subject invention.

In a preferred embodiment, the compounds of the subject invention have the structure shown in FIG. 1. Specific examples of compounds of the subject invention have structures as shown in FIG. 2. The substituents A, B, C, D, and E of the structure shown in FIG. 1 can be as shown in any of the specific structures exemplified herein or can be analogs, derivatives, or salts, so long as the characteristic enzyme inhibitory activity is retained.

In specific embodiments of the subject invention, substituents A–E can be as follows:

A can be $NO_2$, $C_{1-6}$ alkyl, $C_{1-6}$ alkenyl, aryl, heteroaryl, $C_{1-6}$ alkyl $CO_2H$, $C_{1-6}$ alkylaryl, cycloalkyl, or a linker molecule wherein the core structure is linked to another active compound such as, for example cytidine monophosphate, N-acetyl lactosamine or other oligosaccharide.

B can be the same or different from A, or may not be present at all.

C and E, which may be the same or different, may be H, a substituted amine group, such as $NHCH(NH_2)_2$, or $OR^1$ where $R^1$ is H, $C_{1-6}$ alkyl (optionally substituted with —OH), $C_{2-6}$ alkenyl, aryl, heteroaryl, $C_{1-6}$ alkylaryl, cycloalkyl, or a sulfur containing group such as $SO_2$.

D can be $NHR^2$ wherein $R^2$ is $COR^3$ and $R^3$ is $C_{1-6}$ alkyl, $C_{1-6}$ alkenyl, aryl, heteroayl, alkyl-aryl, or cycloalkyl.

As used herein, the term "$C_{1-6}$ alkyl" refers to a straight or branched chain alkyl moiety having from 1 to 6 carbon atoms, including for example, methyl, ethyl, propyl, isopropyl, butyl, t-butyl, pentyl, hexyl, and the like.

The term "$C_{2-6}$ alkenyl" refers to a straight or branched chain alkyl moiety having two to six carbons atoms and having at least one double bond. This term includes, for example, vinyl, one -propenyl, 1- and 2-butenyl, 2-methyl-2-propenyl, and the like.

The term "aryl" refers to an optionally substituted phenyl or naphthyl group with the substituents being selected, for example, from halogen, trifluoromethyl, $C_{1-6}$ alkyl, alkoxy, phenyl and the like. Halogens contemplated within the scope of the invention include fluorine, chlorine, bromine, and iodine.

The term "heteroaryl" refers to an aromatic ring system of 5–10 atoms of which at least one atom is an O, N or S. Included within the scope of this term are, for example, furanyl, thiophenyl, pyridyl, indolyl, quinolyl, and the like.

The term "cycloalkyl"refers to a saturated alicyclic moiety having from three to eight carbon atoms and includes, for example, cyclopropyl, cyclobutyl, cyclopentyl, cyclohexyl and the like.

The term "alkylaryl" refers to an alkyl aryl group wherein the alkyl and the aryl are as described herein.

The term "alkoxy" refers to a straight chain or branch chain alkoxy group containing up to about six carbon atoms, including for example, methoxy, ethoxy, propoxy, isopropoxy, butoxy, tertbutoxy and the like.

Figure 3:
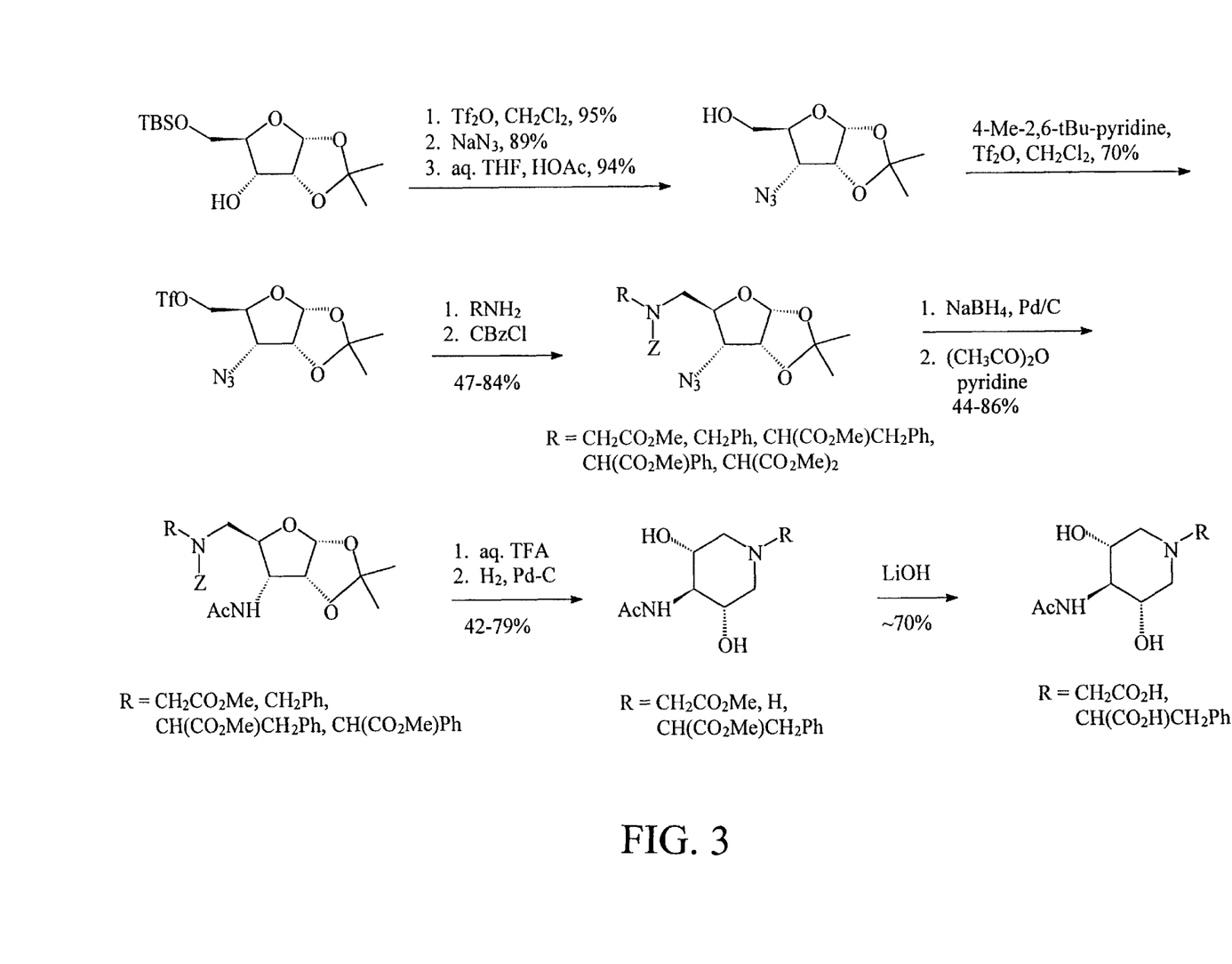
FIG. 3 shows the synthesis of inhibitory N-alkyl piperidines.

A series of N-substituted 3,4,5 trans-trans piperidines have been synthesized by the method shown in FIG. 3. This class of compounds was designed to favorably interact with the enzyme active site via mimicry of the transition states catalyzed by these enzymes.

Figure 4A:
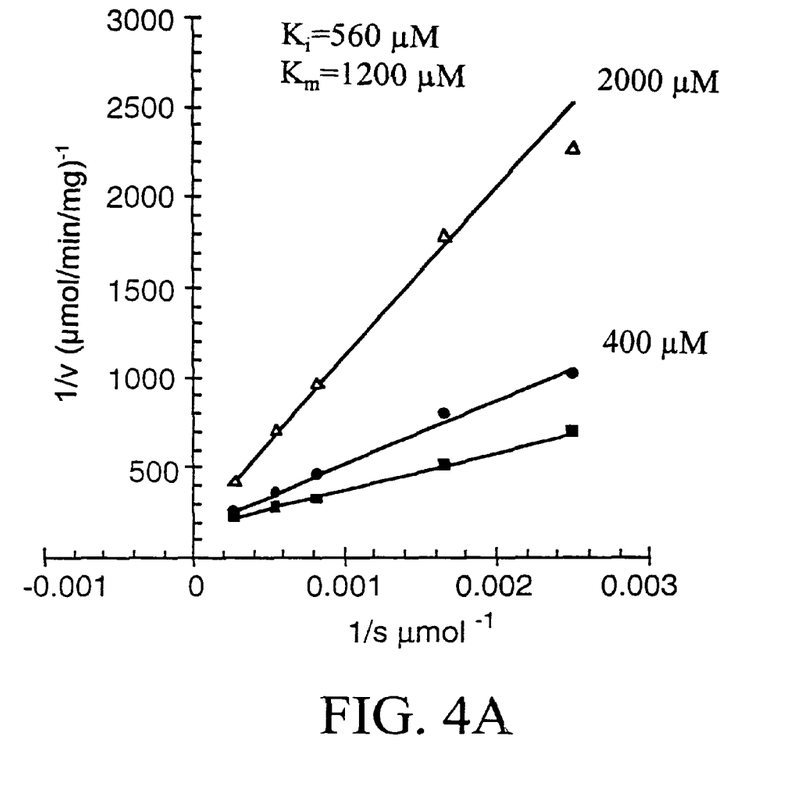
FIG. 4a shows a graph showing inhibition of the *Salmonella typhimurium* neuraminidase.
Figure 4B:
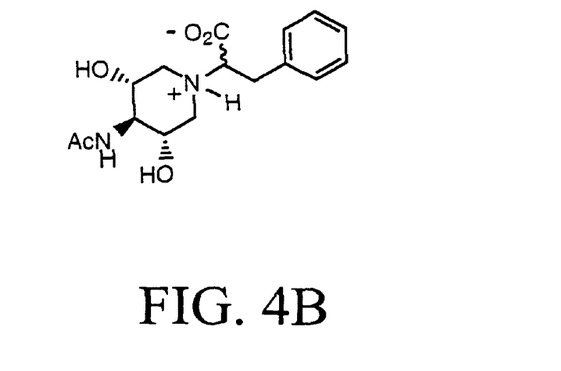
FIG. 4b shows the N-methyl α-carboxy, α-benzyl trans-trans 3,5-dihydroxy, 4-acetamido piperidine compound used for the inhibition.

An example of the inhibitory efficacy of one inhibitor of the subject invention is shown in FIG. 4a; N-methyl α-carboxy, α-benzyl trans-trans 3,5-dihydroxy, 4-acetamido piperidine (FIG. 4b) competitively inhibited the neuraminidase from *Salmonella typhimurium* at a concentration of less than or equal to 550 micromolar concentration.

In a specific embodiment, a series of 5-deoxy-5-N-alkyl 3-deoxy-3-azido xylosides were prepared in good-to-excellentyield via reaction of 5-triflate substituted xylosides with primary amines. Subsequent reductive cyclization by catalytic hydrogenation under neutral conditions lead to trans,trans-4-acetamido-3,5 dihydroxypiperidines 5a and ±5b which were found to be sub-millimolar competitive inhibitors of bacterial sialidases from *S. typhimurium*, and *C. perfringens* even though the inhibitors lacked the C6–C9 glycerol side chain found in the N-acetylneuraminic acid substrate. Inhibitor ±5b, which contains a hydrophobic aglycon mimic, bound tighter than 5a to the *S. typhimurium* and *V. cholerae* sialidases, but no preference was seen between 5a and 5b for the *C. perfringens* sialidase. The results show that inclusion of hydrophobic aglycon mimicry is an effective approach for increasing binding interactions with the *S. typhimurium* and *V. cholerae* sialidases, and is also a means of discriminating between sialidases of different origin.

In another embodiment, the subject invention provides a synthetic route to novel N-functionalized 4-acetamido-2,4-dihydroxypiperidines which allows for the flexible N-substitution based on the starting amine employed. This is a new structural class of sialidase inhibitor which combines transition state analogy with the ability to include aglycon mimicry. These compounds competitively inhibit bacterial sialidases with $K_i$s ranging from $\sim 10^{-4}$–$10^{-3}$ M, despite the lack of the glycerol side chain analogous to the C7–C9 tail of N-acetyl neuraminic acid. The results indicate that 1) location of the oxocarbenium ion charge mimic in a position analogous to the glycosyl carbon, and 2) inclusion of hydrophobic aglycon functionality, are viable strategies for the development of sialidase inhibitors.

The compounds of the subject invention have several advantageous properties. First, the new compounds are acid-stable. Second, the new compounds have a unique mode of interaction with the target neuraminidases;thus, there is a reduced possibility of mutational drug resistance. Third, the compounds of the subject invention have advantageous bioavailability.

In a preferred embodiment, the compounds of the subject invention advantageously inhibit the ability of neuraminidases to cleave the glycosidic bond to N-acetylneuraminic acid in glycoproteins, glycolipids, and oligosaccharides. Microorganisms, viruses, or cells which contain neuraminidases are the targets for these inhibitory compounds. In specific embodiments, the compounds of the subject invention can be used to inhibit the neuraminidase from the influenza virus and/or neuraminidases from bacterial pathogens such as Salmonella, Vibrio, and Clostridium species.

In addition to the application of the new compounds as neuraminidase inhibitors, these compounds can be used as inhibitors of sialyltransferase enzymes and parasitic trans-sialidase enzymes. The former class of enzymes has been strongly implicated in mediation of receptor based cell-cell binding interactions, including processes such as inflammation and metastasis. The trans-sialidases are enzymes found in, for example, *Trypanosoma cruzi*, a microorganism responsible for Chagas' disease, widespread in South America. The basis for application to these other enzymes is that they share in common with neuraminidases the cleavage of bonds to the anomeric carbon of N-acetylneuraminic acid. The inhibitors of the subject invention can be used with neuraminidases, sialyltransferases, and trans-sialidases through a common mode of action.

The inhibitor compounds of the subject invention can also be used to regulate cell-cell interactions, modulate immune response and inflammation, and prevent metastasis.

The compounds of the subject invention can be used by administering, to a person or animal in need of treatment, an effective amount of one or more of the inhibitory compounds. The compounds can also be used to disinfect surfaces.

As used herein, the "effective amount" of a compound of the invention required for use in the methods described herein will vary not only with the particular compound selected but also with the mode of administration, the nature of the condition of the subject, and the age and health of the subject. The exact dosage will ultimately be determined by a physician or other person skilled in the art. However, a suitable dose will generally range from about 0.01 to about 200 mg/kg of body weight per day. More preferably, an effective amount (suitable dose) will range from 0.1 to 50 mg/kg/day.

In the case of administration to reduce or prevent infection, treatment may occur before infection (i.e., prophylaxis), at the start of infection, or after the onset of established symptoms. Treatment with the effective amount may be given 1 to 4 times daily, and the typical duration will range from 3 to 7 days, or until infection is no longer present and/or symptoms have disappeared. Those skilled in the art will recognize that deviations from the above-described treatment methods and effective amounts are possible and are to be included in the subject matter taught herein.

Furthermore, it is possible that, during therapy, the compounds may be administered as pure chemical or a pure pharmaceutically acceptable salt, solvate, hydrate or derivative. However, it is preferable to provide the active chemical, or its pharmaceutical formulation, either as a dry powder (tablet or capsule form or with a suitable carrier), or as a solution or suspension (in water or in physiologically acceptable solvents or cosolvents such as ethanol, propylene glycol, or PEG 400). The appropriate pharmaceutical formulation may be administered by oral, intranasal, intravenous, intramuscular, or other appropriate modes. The desired dosage (effective amount) may be administered in one or in divided doses at appropriate intervals each day. The compounds and compositions of the invention may also be administered in combination with other therapeutic agents. Those skilled in the art will appreciate that dosages and modes of administration are readily determinable without undue experimentation.

MATERIALS AND METHODS

Starting materials and reagents were purchased from Sigma, Aldrich or Fisher Scientific, and were used without further purification. Sialidases from *Salmonella typhimurium*, *Clostridium perfringens*, and *Vibrio cholerae* were purchased from Sigma. Solvents were obtained from Fisher Scientific as A.C.S. reagent grade. THF was dried immediately before use by distillation from Na/benzophenone under nitrogen. Moisture sensitive reactions were performed under an atmosphere of nitrogen using standard techniques. Analytical TLC was performed on silica gel 60F-245 plates. Column chromatography was performed with Davisil grade 633 type 60 A, silica gel (200–425 mesh). Chemical ionization methods, (CI) used either ammonia, or isobutane, FAB-MS used nitrobenzyl alcohol as matrix. NMR and other spectral data for all compounds are presented in the Supporting Information section.

Following are examples which illustrate procedures for practicing the invention. These examples should not be construed as limiting. All percentages are by weight and all solvent mixture proportions are by volume unless otherwise noted.

EXAMPLE 1

Synthetic Procedures

Figure 5:
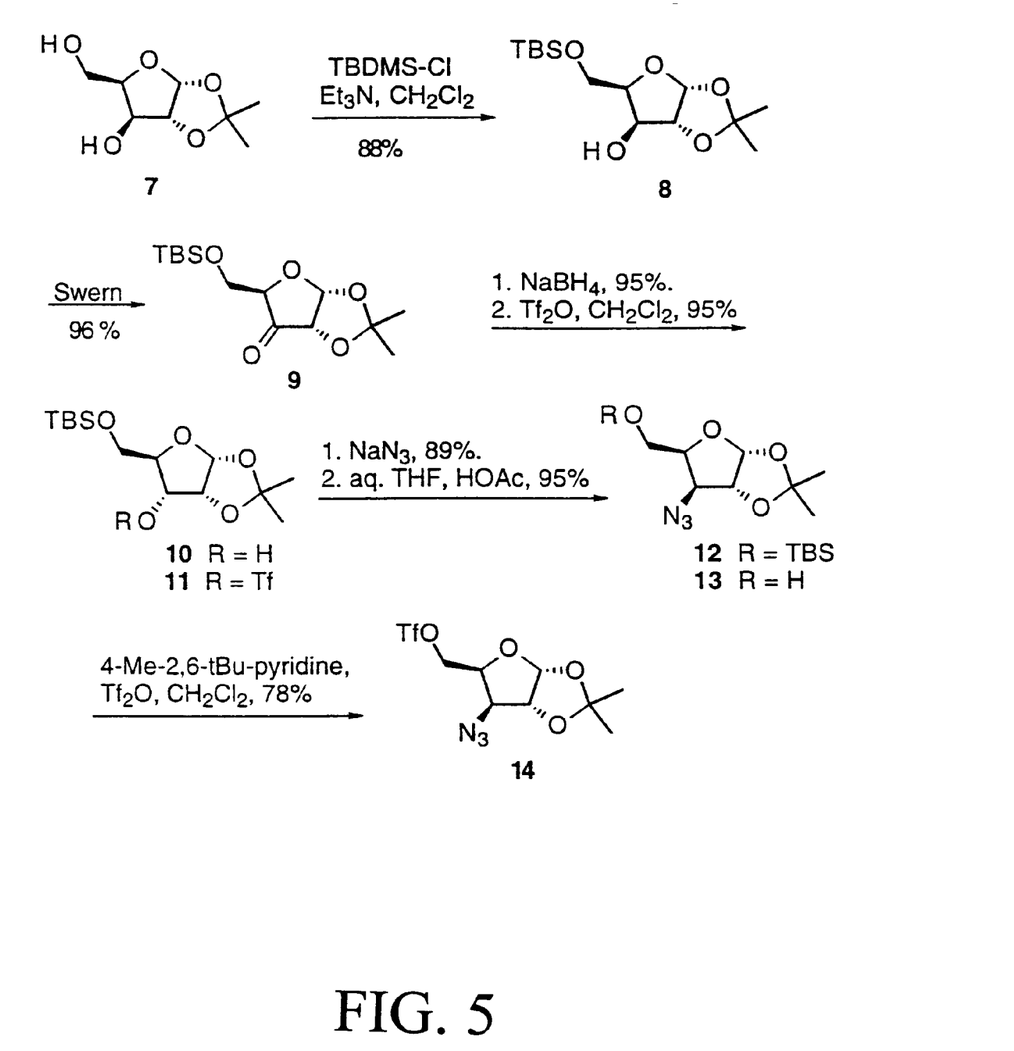
FIG. 5 is a scheme showing synthesis of certain compounds according to the subject invention.
Figure 6:
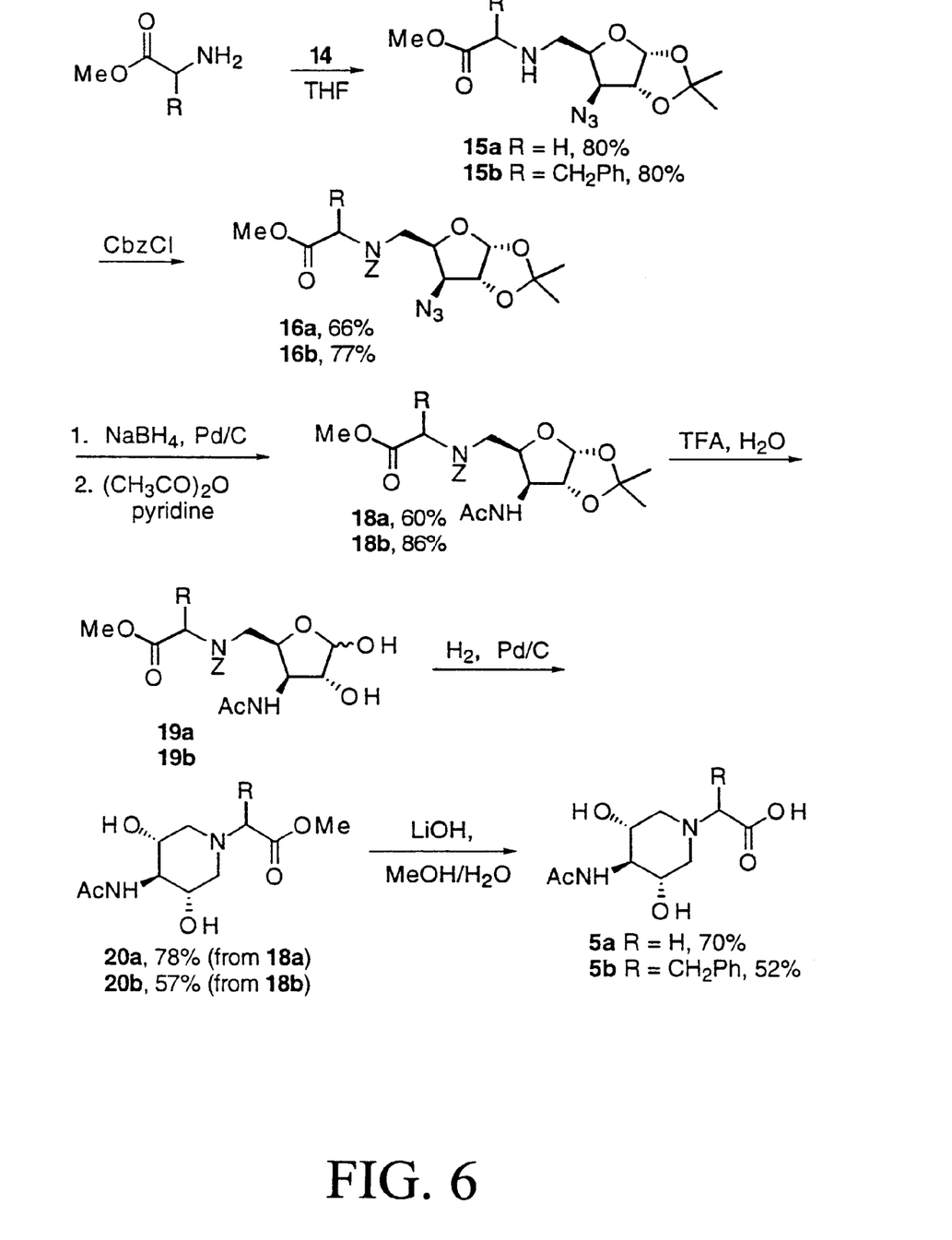
FIG. 6 is a scheme showing synthesis of certain compounds according to the subject invention.

The synthesis of the trans, trans 3,5 dihydroxy 4-acetamido piperidines compounds 5a and ±5b in FIG. 6 was based on the plan that reductive cyclization of a 5-N-alkyl xylose derivative (compound 19, FIG. 6) would readily afford piperidines with the desired relative stereochemistry; the 5-N-alkyl xylose compounds would be prepared by N-alkylation of primary amines with a xyloside derivatized at C-5 for nucleophilic displacement, as outlined in FIG. 5.

The synthesis started from 1,2-isopropylidene-a-D-xylofuranose (a similar transformation of a 1,2 isopropylidene xylofuranoside to the ribofuranoside has been reported: Ritzmann, G.; Klein, R. S.; Hollenberg, D. H.; Fox, J. J. *Carb. Res.* 1975, 39, 227–236) 7, (FIG. 5), which was selectively protected in 94% yield as the t-butyldimethylsilyl ether 8. The stereochemistry of the secondary alcohol was then inverted by Swern oxidation (Mancuso, A. J.; Huang, S.-L.; Swem, D. *J. Org. Chem.* 1978, 43, 2480–2482) to the ketone 9, and stereoselective reduction (Sour, W.; Thomas, G. H. S. *Can. J. Chem.* 1966, 44 836–837) with NaBH$_4$ to ribofuranoside 10.

The required xylo-stereochemistry for azide 12 can be obtained by displacement of a suitable derivative of the C-3 hydroxyl in alcohol 10. Reaction of ribotriflate 11 (obtained from 10 by reaction with triflic anhydride and pyridine), with sodium azide afforded the protected azide 12 in 85% yield from 10. Unlike the reported reaction for the corresponding xylotriflate, no elimination products were observed (Ozols, A. M., Azhayer, A. V., Dyatkina, N. B., Krayezsky, A. A. *Synthesis* 1980 557–559; Ozols, A. M., Azhayer, A. V., Krayezsky, A. A., Ushakov, A. S., Gnuchev, N. V., Cortikh, B. P. *Synthesis* 1980, 559–561). The xylo-configuration of azide 12 was established by X-ray crystallographic analysis of a diacetyl derivative (obtained by reduction of azide 12 to the amine with Raney nickel, N-acetylation, desilylation, and O-acetylation).

Desilylation of 12 afforded alcohol 13, which was then converted to the triflate 14. The hindered base 2,6-di-tert-butyl-4-methylpyridine had to be used in order to obtain the triflate in high yield (Binkley, R. W.; Ambrose, M. G. *J. Carb. Chem.* 1984, 3, 1–49). Triflate 14 was sufficiently stable to purify it by column chromatography on silica, but decomposed slowly at 4° C., and so was used immediately after purification. The synthesis of the key intermediate azidotriflate 14 from commercially available 1,2-isopropylidenea-D xylose was achieved in 44% overall yield for 7 steps, and can be prepared at the gram scale.

The purified triflate 14 was converted to the secondary amines 15a,b by displacement with glycine methyl ester and D/L phenylalanine methyl ester, respectively (Yenakis, D.; Moll, N.; Gross, B. *Synthesis* 1983, 541–542), as shown in FIG. 6. The displacements proceeded smoothly at room temperature, with yields of 80% for 15a,b. Amines 15a,b were then protected as the CBZ carbamates 16a,b in 66–89% yields (Scwarz, H.; Bumpas, F. M.; Page, I. H. *J. Am. Chem. Soc.* 1957, 79 5697–5703).

The azides 16a,b were then reduced (Kokotos, G.; Constantinou-Kokotou, V. *J. Chem. Res.* mini print JRM-FDQ p311 (1992)) to the corresponding amines 17a,b which were acetylated to give the 3-acetamido furanosides 18a,b in 60% and 86% overall yields from 16a,b. The 1,2 isopropylidene ketal of compounds 18a,b was hydrolyzed to provide the hemiacetals 19a,b as a mixture of a- and b-anomers. It is preferable to carry out the hydrolytic removal of the isopropylidene group with the secondary amine blocked as the benzyl carbamate. Acid hydrolysis of the ketal in analogous N-unprotected compounds afforded products which appeared to have aromaticized. Their aromatic nature was evident from $^1$H-NMR spectra which showed a multiplet at d7.5–8.0 ppm consisting of 4 hydrogens. The hemiacetals 19a,b were then reductively cyclized under neutral conditions to give the piperidines 20a,b in 78% and 57% yields from 18a,b. Compounds 20a,b were converted to the sialidase inhibitors 5a, ±5b by alkaline hydrolysis in 70% and 52% respective yields after chromatography.

1,2-O-Isopropylidene-5-O-t-butyldimethylsilyl-a-D-xylofuranose (8). 1-2-O-isopropylidene-D-xylofuranose (7.608 g, 40 mmol) was dissolved in CH$_2$Cl$_2$ (120 ml) and cooled in an ice bath. Triethylamine (7.8 ml, 56 mmol) and TBDMSCl (7.3 g, 48 mmol) were added. The reaction was stirred at 0° C. for 30 mins, then warmed to room temperature and stirred for 18 hrs at which time additional triethylamine (0.7 ml, 5 mmol) and TBDMSCl (0.7 g, 4.6 mmol) were added to the reaction mixture with stirring continued for 5 hours. The reaction mixture was concentrated in vacuo, and the residue suspended in CH$_2$Cl$_2$ (40 ml) and filtered. CHCl$_3$ (120 ml) was added and the solution was washed with IM HCl (4×30 ml), saturated aqueous NaCl (1×30 ml), dried (Na$_2$SO$_4$). Chromatography on silica (1% methanol in CHCl$_3$) afforded compound 8 (10.77 g, 88%) as an oil. $^1$H NMR analysis of 8 showed a small amount of di-silylated product which was removed in the next step of the synthesis. [a]$_D^{20}$ –9.3° (c=10 g/100 mL, CHCl$_3$); FAB HRMS exact mass calcd. for MH$^+$ C$_4$H$_{29}$SiO$_5$ requires 305.1784, found 305.1784.

1,2-O-Isopropylidene-3-oxo-5-O-t-butyldimethylsilyl-D-xylofuranose (9). Oxalyl chloride (3.4 ml, 39 mmol) was dissolved in dry CH$_2$Cl$_2$ (105 ml), and cooled to −55° C. DMSO (5.5 ml, 77.9 mmol) was added such that the temperature remained below −50° C. and the mixture was stirred for 2 minutes. A solution of compound 8 (10.77 g, 35.4 mmol) in dry CH$_2$Cl$_2$ (35 ml), was added slowly over 5 minutes and the mixture was stirred at −50° C. for 30 minutes. Triethylamine (16.3 ml, 117 mmol) in dry CH$_2$Cl$_2$ (30 ml), was added and the mixture stirred at −55° C. for a further 40 minutes. The reaction mixture was warmed to rt, stirred for 2.5 hours, then poured into 160 mL of water and extracted with CHCl$_3$ (130 ml). The organic layer was then washed with saturated aqueous NaCl (1×80 ml) and dried over Na$_2$SO$_4$. The crude product was crystallized from hexane to give compound 9 as a waxy solid: (10.3 g, 96%); mp 32° C.; [a]$_D^{20}$+114° (c=10 g/100 mL, CHCl$_3$); FAB HRMS exact mass calcd. for MH$^+$ C$_{14}$H$_{27}$SiO$_5$ requires 303.1627, found 303.1599.

1,2-O-Isopropylidene-5-O-tertbutyldimethylsilyl-D-ribofuranose (10). Ketone 9 (6.89 g, 22.8 mmol) was dissolved in ethanol (150 ml) and water (50 ml) and cooled in an ice bath. NaBH$_4$ (5.61 g, 148.3 mmol) was then added and stirring was continued for 3.5 hours. The reaction mixture was poured into water (400 ml), extracted with ethyl acetate (8×150 ml). The combined organic layers were then dried (Na$_2$SO$_4$), and concentrated in vacuo to afford 10 (6.60 g, 95%); [a]$_D^{20}$+25.7° (c=4.1 g/100 mL, CHCl$_3$).

1,2-O-Isopropylidene-3-trifluoromethanesulfonyloxy-5-O-t-butyldimethylsilyl-D-ribofuranose (11). Triflic anhydride (1.8 ml, 10.6 mmol) was dissolved in 15 mL of dry (CH$_2$Cl)$_2$ and added to a solution of pyridine (1.2 ml, 15.6 mmol) in 10 mL of (CH$_2$Cl)$_2$ at −10° C. After 3 minutes a precipitate formed. A solution of 10 (3.2 g, 10 mmol) in 16 mL of(CH$_2$Cl)$_2$ was added at −10° C. and stirred for 2.25 hours at this temperature. Aqueous 5% NaHCO$_3$ (40 ml) was added, the reaction was warmed to rt and stirred for 30 minutes before being cast into CHCl$_3$ (60 ml). The organic phase was washed with 5% NaHCO$_3$ (40 ml), saturated aqueous NaCl (30 ml), then dried (Na$_2$SO$_4$). After concentrated in vacuo, the residue was dissolved in toluene (50 ml) and re-evaporated; this procedure was repeated 3 times providing the triflate 11 (4.33 g, 95%) as a red oil.

1,2-O-Isopropylidene-3-deoxy-3-azido-5-O-tertbutyldimethylsilyl-D-xylofuranose (12). Triflate 11 (4.33 g, 10 mmol) was dissolved in a suspension of NaN$_3$ (3.75 g, 57.7 mmol, in 50 mL of ethanol) at rt. The reaction was heated to 65–70° C. for 14 hours, after which time additional NaN$_3$ (3.75 g, 57.7 mmol) was added followed by reflux for 24 hours. The reaction was then cooled to rt and stirred for 4 days. The reaction mixture was concentrated, and was then partitioned between water (30 ml) and CHCl$_3$ (100 ml). The organic fraction was then washed with water (2×30 ml), saturated aqueous. NaCl (1×30 ml), and dried (Na$_2$SO$_4$). Column chromatography on silica gel (4:6 hexane/CHCl$_3$) afforded azide 12 (2.912 g, 89%) as an oil. FAB HRMS exact mass calcd. for MH$^+$ C$_{14}$H$_{28}$SiN$_3$O$_4$ requires 330.1849, found 330.1824.

1,2-O-Isopropylidene-3-deoxy-3-azido-D-xylofuranose (13). The azide 12 (1.84 g, 5.6 mmol) was dissolved in 20 mL of 50% aqueous THF, and CH$_3$COOH (15 ml) was added. The reaction was stirred (rt, 18 h), then carefully quenched by the addition of water (60 ml) and sufficient Na$_2$CO$_3$ to raise the pH above 9. The mixture was extracted with CHCl$_3$ (3×30 ml), and the combined organic phases were dried (Na$_2$SO$_4$). Column chromatography on silica gel (1:3 ethyl acetate/hexane)afforded alcohol 13 (1.14 g, 95%) as an oil. [a]$D^{20}$−44° (c=3.87 g/100 mL, CHCl$_3$); FAB HRMS exact mass calcd. for MH$^+$ C$_8$H$_{14}$N$_3$O$_4$ requires 216.0984, found 216.1016.

1,2-O-Isopropylidene-3-deoxy-3-azido-5-trifluoromethanesulfonyloxy-D-xylofuranose (14). 4-Methyl-2,6-di-t-butylpyridine (1.28 g, 6.3 mmol) was dissolved in 10 mL of dry (CH$_2$Cl)$_2$ under N$_2$ and then cooled to −78° C. Triflic anhydride (1.05 ml, 6.3 mmol) was added to the solution which was then stirred for 5 minutes. A solution of 13 (1.12 g, 5.2 mmol) in 12 mL of dry (CH$_2$Cl)$_2$ was added to the triflate solution which was then stirred at −10° C. for 30 minutes. The reaction was warmed to rt, 10 mL of hexane was added, and the solution loaded onto a silica gel column. Elution with 3:7 hexane/CHCl$_3$ afforded triflate 14 (1.41 g, 78%). FAB HRMS exact mass calcd. for MH$^+$ C$_9$H$_{13}$SN$_3$F$_3$O$_6$ requires 348.0477, found 348.0477.

1,2-O-Isopropylidene-3,5-dideoxy-3-azido-5-N-(1'-carbomethoxy-ethyl)-D-xylofuranose (15a). Triflate 14 (1.41 g, 4.05 mmol) was dissolved in 10 mL of dry THF, and glycine methyl ester (1.36 g, 15.3 mmol) in 12 mL of THF was added and the reaction stirred at rt for 14.5 h. The reaction mixture was concentrated in vacuo and the crude product was then purified by column chromatography on silica gel (1:1 hexane/ethyl acetate) to provide 15a (0.93 g, 80%) as a yellow oil. [a]$_D$20–33° (c=5 g/100 mL, CHCl$_3$); FAB HRMS exact mass calcd. for MH$^+$ C$_{11}$H$_{19}$N$_4$O$_5$ requires 287.1355, found 287.1354.

1,2-O-Isopropylidene-3,5-dideoxy-3-azido-5-N-(1'-carbomethoxy-2'-benzyl-ethyl)-D-xylofuranose (15b). Prepared as 15a, using 14 (3.94 mmol) in 7.9 mL of THF and DL-phenylalanine methyl ester (1.41 ml 7.88 mmol) in THF (20 ml). Work up as 16a and column chromatography(1:3 ethyl acetate/hexane)gave 15b (1.19 g, 80%) as an oil; FAB HRMS exact mass calcd. for MH$^+$ C$_{18}$H$_{25}$N$_4$O$_5$ requires 377.1825, found 377.1825.

1,2-O-Isopropylidene-3,5-dideoxy-3-azido-5-N-(1'-carbomethoxy-ethyl)-5-N-benzyloxycarbonyl-D-xylofuranose (16a). The amine 15a (0.92 g, 3.2 mmol) was dissolved in 18 mL of dioxane and cooled in an ice bath. Na$_2$CO$_3$ (2.19 g, 17.7 mmol) in 54 mL of water was added to this solution, followed by dropwise addition of benzyl-chloroformate (4.57 ml, 32 mmol) to the rapidly stirred mixture. The reaction was then stirred at rt for 17*h*. The mixture was poured into 10% Na$_2$CO$_3$ (100 ml), and extracted with ethyl acetate (4×50 ml). The combined organic fractions were dried (Na$_2$SO$_4$) and concentrated in vacuo. The crude product was then purified twice by column chromatography on silica gel(8:2 hexane/ethyl acetate, then 4% methanol in toluene) to afford 16a (0.893 g, 66%) as an oil; [a]$_D^{20}$ −37° (c=5 g/100 mL, CHCl$_3$); FAB HRMS exact mass calcd. for MH$^+$ C$_{19}$H$_{25}$N$_4$O$_7$ requires 421.1723, found 421.1705.

1,2-O-Isopropylidene-3,5-dideoxy-3-azido-5-N-(1'-carbomethoxy-2'-benzyl-ethyl)-5-N-benzyloxycarbonyl-D-xylofuranose (16b). Prepared as for 16a, using the amine 15b (1.161 g, 3.095 mmol) in 100 mL of dioxane and 50 mL of water, with Na$_2$CO$_3$ (0.826 g, 7.72 mmol), and CbzCl (0.97 ml, 6.79 mmol). Work up and purification as for 16a gave the product 16b (1.218 g, 77%) as an oil; FAB HRMS exact mass calcd. for MH$^+$ C$_{26}$H$_{31}$N$_4$O$_7$ requires 511.2193, found 511.2205.

1,2-O-Isopropylidene-3,5-dideoxy-3-amino-5-N-(1'-carbomethoxy-ethyl)-5-N-benzyloxycarbonyl-D-xylofuranose (17a). 10% Pd/C (1 mg per 6 to 10 mg of azide 16) was suspended in water, and to it a solution of azide 16a (0.707 g, 1.68 mmol) in 16 mL of methanol was added. NaBH$_4$ (0.191 g, 5.05 mmol) was added in three portions over 15 minutes at rt. After stirring for a further 30 minutes, the reaction mixture was filtered through celite. The celite was washed with methanol (1 reaction volume) and water (10 reaction volumes). The pH of the combined filtrates was adjusted to pH 7 with 1 M HCl and the methanol removed under reduced pressure. The aqueous layer was then adjusted to pH 1 and washed with ethyl acetate (2×25 mL), basicified to pH 10 with 10% $Na_2CO_3$, extracted with $CHCl_3$ (6×30 mL), basicified to pH 12 with NaOH, and extracted with ethyl acetate (4×20 mL). The organic extracts were combined, dried ($Na_2CO_3$), then concentrated in vacuo, to yield the crude amine 17a as an oil which was used immediately without further purification.

1,2-O-Isopropylidene-3,5-dideoxy-3-azido-5-N-(1'-carbomethoxy-2'-benzyl-ethyl)-5-N-benzyloxycarbonyl-D-xylofuranose (17b). Amine 17b was prepared from azide 16b (0.844 g, 1.65 mmol) according to the method above for 17a using methanol (10 ml), water (40 ml), Pd/C (130 mg), and $NaBH_4$ (188 mg, 4.96 mmol). Workup as for 17a afforded 17b as an oil which was used immediately without further purification.

1,2-O-Isopropylidene-3,5-dideoxy-3-acetamido-5-N-(1'-carbomethoxyethyl)-5-N-benzyloxycarbonyl-D-xylofuranose (18a). The crude amine 17a (663 mg, 1.68 mmol) was dissolved in 20 mL of 1:1 (v/v) dry pyridine/acetic anhydride and stirred for 3 hours. The reaction mixture was concentrated under reduced pressure, and the residue was dissolved in ethyl acetate (50 ml). This was washed with 10% $Na_2CO_3$ (3×20 ml), 1 M HCl (3×20 ml), saturated NaCl (1×10 ml), then dried ($Na_2SO_4$), to yield the N-acetate 18a (443 mg, 60% from 16a) as an oil: FAB HRMS exact mass calcd. for $MH^+$ $C_{21}H_{29}N_2O_8$ requires 437.1924, found 437.1924.

1,2-O-Isopropylidene-3,5-dideoxy-3-acetamido-5-N-(1'-carbomethoxy-2'-benzylethyl)-5-N-benzyloxycarbonyl-D-xylofuranose (18b). Amine 17b was dissolved in dry pyridine (40 ml) and dry acetic anhydride (50 ml) and stirred for 17 hours at rt. Work up and isolation as for 18a, and column chromatography (7:3 ethyl acetate/hexane) afforded N-acetate 18b (747 mg, 86% from 16b) as a white solid, with partial separation of the diastereoisomers: diastereoisomer A 314 mg, diastereoisomer A+B 267 mg, diastereoisomer B 166mg; Isomer A mp54–56° C.; FAB HRMS exact mass calcd. for $MNa^+$ $C_{28}H_{34}NaN_2O_8$ requires 549.2213, found 549.2227. $MH^+$ $C_{28}H_{35}N_2O_8$ requires 527.2393, found 527.2369. Isomer B MP 60–61° C. $MH^+$ $C_{28}H_{35}N_2O_8$ requires 527.2393, found 527.2379; MNa+ $MNa^+$ $C_{28}H_{34}NaN_2O_8$ requires 549.2213, found 549.2249.

1,2-dihydroxy-3,5-dideoxy-3-acetamido-5-N-(1'-carbomethoxy-ethyl)-5-N-benzyloxycarbonyl-D-xylofuranose (19a). The acetate 18a (200 mg, 0.45 mmol) was dissolved in TFA (2.27 ml) at 0° C., and water (0.5 ml) was added dropwise. The reaction was stirred (0° C., 18 h) then warmed to rt, and cautiously neutralized (9 g $Na_2CO_3$ in 80 mL water). This solution was then extracted with ethyl acetate (8×25 ml). The combined organic fractions were dried ($Na_2SO_4$) and concentrated in vacuo to afford crude 19a as an oil: 181 mg, quantitative. Hemiacetal 19a was then used immediately in the next step.

1,2-Dihydroxy-3,5-dideoxy-3-acetamido-5-N-(1'-carbomethoxy-2'-benzyl-ethyl)-5-N-benzyloxycarbonyl-D-xylofuranose (19b). The acetate 18b (267 mg, 0.51 mmol) was dissolved in TFA (4.5 ml) at 0° C., and water (0.5 ml) was added dropwise. The reaction was then stirred between 0° C. and +4° C. for 21 hours before cautiously being added to a solution of $Na_2CO_3$ (6.88 g, 64.9 mmol) in water (60 ml). The solution was then extracted with ethyl acetate (4×40 ml). The combined organic fractions were dried ($Na_2SO_4$) and concentrated in vacuo. Column chromatography on silica gel (step gradient; 6% to 10% methanol in $CHCl_3$) afforded 19b (173 mg, 70%) as an oil which was used immediately for synthesis of 20b.

trans-trans-N-(1'-carbomethoxy-ethyl)-3,5-dihydroxy-4-acetamidopiperidine (20a). The hemiacetal 19a (181 mg, 0.46 mmol) was dissolved in 60 mL of methanol and 10% Pd/C (200 mg), added. This solution was then hydrogenated using a Parr hydrogenation apparatus (rt, 48 psi, 17 h). The solution was filtered through celite and concentrated in vacuo. Recrystallizationonce from ethyl acetate/hexane and once again from ethanol/diethyl ether afforded 20a (87 mg, 78%) as a white solid: mp 133–136° C.; FAB HRMS exact mass calcd. for $MH^+$ $C_{10}H_{19}N_2O_5$ requires 247.1294, found 247.1273.

(±)-trans-trans-N-(1'-carbomethoxy-2'-benzyl-ethyl)-3,5-dihydroxy-4-acetamidopiperidine (±20b). The hemiacetal 19b (173 mg, 0.35 mmol) was dissolved in methanol (17 ml), and Pd/C (150 mg), added. This solution was then hydrogenated using a Parr hydrogenation apparatus at ambient temperature and 46 psi $H_2$ for 25 hrs. The solution was filtered through celite, washed well with methanol and concentrated in vacuo. Column chromatography on silica (8% methanol in $CHCl_3$) afforded 20b (95 mg, 81%) as a white solid: mp 156–159° C.; FAB HRMS exact mass calcd. for $MH^+$ $C_{17}H_{25}N_2O_5$ requires 337.1763, found 337.1768.

trans-trans-5-N-(1'-carboxy-ethyl)-3,5-dihydroxy-4-acetamidopiperidine (5a). Ester 20a (25 mg, 0.1 mmol) was dissolved in 1 mL of 80% methanol /water, and $LiOH.H_2O$ (17 mg, 0.4 mmol) was added. The reaction was stirred at rt for 35 minutes, then 1M HCl was added dropwise to lower the pH to 1. Concentration in vacuo gave the crude product 5a. This was purified by column chromatography on silica gel (7:2 isopropanol:water), to give the product 5a (19 mg, 70%) as a white solid: mp 230–234° C.; FAB HRMS exact mass calcd. for $MH^+$ $C_9H_{17}N_2O_5$ requires 233.1137, found 233.1138.

trans-trans-5-N-(1'-carboxy-benzyl-ethyl)-3,5-dihydroxy-4-acetamidopiperidine (±5b). Methyl ester ±20b (18 mg, 0.05 mmol) was dissolved in water (0.15 ml), methanol (0.60 ml), and $LiOH.H_2O$ (2.5 mg, 0.06 mmol) added. After stirring at rt for 48 hours, the reaction mixture was concentrated to near dryness in vacuo. The residue was dissolved in 10 mL of water (pH adjusted to 6), then purified on Amberlite 120 ($H^+$ form) by initial elution with water followed by a step gradient of 2 to 5% $NH_4OH$. The product bearing fractions were combined and concentrated under reduced pressure to give ±5b (9.5 mg, 52%) as a white solid: mp 195–19° C.; FAB HRMS exact mass calcd. for $MNa^+$ $C_{16}H_{22}N_2O_5Na$ requires 345.1426, found 345.1486.$MH^+$ $C^{16}H_{23}N_2O_5$ requires 323.1607, found 323.1607.

EXAMPLE 2

Inhibition Studies

Inhibition constants for 5a and ±5b were determined for sialidases from *Salmonella typhimurium, Clostridium perfringens,* and *Vibrio cholerae* using 2-O-(p-nitrophenyl)-a-D-N-acetylneuraminic acid as substrate at 30°±0.2° C. (Table 1) (Eschenfelder, V.; Brossmer, R. *Carb. Res.* 1987, 162, 294–297). The reaction buffers employed for the three enzymes were, respectively, 50 mM Na-acetate, 100 mM NaCl, pH 5.5; 25 mM Na-acetate, pH 5.5; and 100 mM Na-acetate, 150 mM NaCl, 4 mM $CaCl_2$, pH 5.5. Reaction mixtures (700 mL) consisted of the appropriate buffer system containing substrate over a range bracketing $K_m$, and different concentrations of inhibitor 5a or ±5b. Each reaction was initiated by addition of 2–5 mU of sialidase, followed by removal of time point aliquots at 5,10, and 15 minutes. Each aliquot was added to 800 mL of 100 mM $Na_2CO_3$, pH 10, and the absorbance at 400 nm due to p-nitrophenolate (e=19,200)determinedto calculate the initial velocity. Data for initial velocity was obtained in duplicate measurements of each substrate/inhibitor concentration. $K_i$s were estimated by non-linear least-squares fit of the initial velocity data to the equation for competitive inhibition.

TABLE 1

Inhibition of bacterial sialidases by 5a and ±5b at pH 5.5, 30° C.

| Sialidase | 5a, $K_i$, mM | ±5b, $K_i$, mM | $K_m$, mM[a] |
|---|---|---|---|
| Salmonella typhimurium | 2500 ± 400 | 560 ± 30 | 1200 ± 100 |
| Clostridium perfringens | 400 ± 100 | 500 ± 70 | 280 ± 30 |
| Vibrio cholerae | >2000[b] | 1500 ± 200 | 2700 ± 740 |

The values for $K_m$ and $K_i$ were determined by fitting initial velocity data obtained at various substrate/inhibitor concentrations to the equation for competitive inhibition.
[a]$K_m$ values are for 2-O-(p-nitrophenyl)-a-D-N-acetylneuraminic acid as substrate.
[b]No inhibition of the V. cholerae sialidase was observed up to 2 mM 5a.

Compounds 5a, 5b represent the core structure of a sialic acid oxocarbenium ion analog, lacking the C6–C9 glycerol side chain found in the natural sialidase substrates and p-nitrophenyl glycoside substrate employed in this work. Despite this, the data presented in Table 1 show that significant inhibition may be obtained, particularly for ±5b. For both the S. typhimurium and V. cholerae sialidases, ±5b binds approximately 2× tighter than the p-nitrophenyl glycoside substrate, while for the C. perfringens sialidase 5a and 5b are bound with slightly lower affinity than substrate. The $K_i$s for 5a and +5b are modest, being in the $10^{-4}$–$10^{-3}$ M range. Inhibitors 5, which lack a glycerol side chain, can be used as a basis for more potent sialidase inhibitors containing a side chain.

The three sialidases tested show different sensitivity to the presence of a hydrophobic aglycon mimic in the inhibitor. The inhibition data suggest that the active site of the C. perfringens enzyme can accommodate a relatively large hydrophobic group (i.e. the phenyl ring of 5b) but that no net energetic advantage over binding 5a exists. Inhibitors 5a/5b bind weakly to the V. cholerae sialidase, though the measurable $K_i$ for 5b suggests that it may benefit from a modest hydrophobic binding effect relative to 5a. This is in contrast to the results for the S. typhimurium enzyme, which binds 5b almost 5 times more tightly than 5a which demonstrates that favorable hydrophobic interactions may indeed be utilized as a component of inhibitor design for the S. typhimurium sialidase.

FIG. 4 presents a double reciprocal plot for the inhibition of the S. typhimurium sialidase by ±5b, from which it is concluded that the inhibition is competitive; the remaining inhibitor/sialidase inhibition kinetics were also well fit to competitive inhibition patterns. The C. perfringens sialidase is inhibited to the same extent by 5a or ±5b whereas the S. typhimurium enzyme binds the more hydrophobic ±5b almost 5 times more tightly than 5a. Compound 5a is did not show inhibition at concentrations below 2 mM, and ±5b was a modest inhibitor of the V. cholerae sialidase, with $K_i$=1.5 mM.

It should be understood that the examples and embodiments described herein are for illustrative purposes only and that various modifications or changes in light thereof will be suggested to persons skilled in the art and are to be included within the spirit and purview of this application and the scope of the appended claims.

We claim:
1. A compound of the formula I wherein
A is selected from the group consisting of $NO_2$, $C_{1-6}$ alkyl, $C_{1-6}$ alkenyl, aryl, $C_{1-6}$ alkyl $CO_2H$, $C_{1-6}$ alkyl-aryl, and cycloalkyl;
B can be the same or different from A or, optionally, is not present at all;
C and E, which are, optionally, the same or different, are selected from the group consisting of substituted or unsubstituted amines, substituted or unstubstituted $C_{1-6}$ alkyl, $SO_2$, and $OR^1$ where $R^1$ is H, $C_{1-6}$ alkyl (optionally substituted with —OH), $C_{2-6}$ alkenyl, aryl, $C_{1-6}$ alkylaryl, or cycloalkyl; and
D is selected from the group consisting of $NHR^2$ wherein $R^2$ is $COR^3$ and $R^3$ is ($C_{1-6}$ alkyl, $C_{1-6}$ alkenyl, unsubstituted aryl, alkyl-aryl, or cycloalkyl;
or a pharmaceutically acceptable salt, solvate, or hydrate thereof.

2. The compound according to claim 1, wherein A is selected from the group consisting of $CH_2CO_2H$, $NO_2$, and $CH(CO_2H)CH_2$ phenyl.

3. The compound according to claim 1, wherein C and E are independently selected from the group consisting of H, $C_{,1-6}$ alkyl, $C_{2-6}$ alkenyl, or $OR^1$ where $R^1$ is H, $C_{1-6}$ alkyl or $C_{2-6}$ alkenyl.

4. The compound according to claim 1, wherein D is NHAc.

5. The compound according to claim 1, selected from the group consisting of 5-N-(1'-carboxy-benzyl-ethyl)-3,5-dihydroxy-4-acetamidopiperidine, and 5-N-(1'-carboxy-ethyl(-3,5-dihydroxy-4-acetamidopiperidine.

6. The compound according to claim 1, wherein C or E is $NHCH(NH_2)_2$.

7. A pharmaceutical composition comprising a compound of claim 1 and a pharmaceutically acceptable diluent or carrier, wherein said compound is present in an amount which is sufficient to inhibit the enzymatic activity of neuraminidase.

8. A method for treating a bacterial infection in a human or animal, said method comprising administering an effective anti-bacterial amount of a compound of claim 1 to said human or animal, wherein said compound treats said infection by inhibiting the enzymatic glycosyltransfer of N-acetylneuramic acid.

9. The method according to claim 8, wherein said bacterial infection is caused by a bacterial pathogen selected from the group consisting of Salmonella, Vibrio, and Clostridium.

10. A method for treating a viral infection in a human or animal, said method comprising administering an effective anti-viral amount of a compound of claim 1 to said human or animal, wherein said compound treats said infection by inhibiting the enzymatic glycosyltransfer of N-acetylneuramic acid.

11. A method for treating a parasitic infection in a human or animal, said method comprising administering an effective anti-parasitic amount of a compound of claim 1 to said human or animal, wherein said compound treats said infection by inhibiting the enzymatic glycosyltransfer of N-acetylneuramic acid.

12. The method according to claim 8, wherein said viral infection is caused by influenza virus.

13. The method according to claim 11, wherein said parasitic infection is caused by the pathogen parasite Trypanosoma.

* * * * *

UNITED STATES PATENT AND TRADEMARK OFFICE
CERTIFICATE OF CORRECTION

PATENT NO. : 6,020,344

DATED : February 1, 2000

INVENTOR(S) : Benjamin A. Horenstein and Ian B. Parr

It is certified that error appears in the above-identified patent and that said Letters Patent is hereby corrected as shown below:

Column 14, line 26: "unstubstituted" should read --unsubstituted--.

Column 14, line 31: "is ($C_{1-6}$ alkyl," should read --is $C_{1-6}$ alkyl,--.

Column 16, line 1: "8" should read --10--.

Signed and Sealed this

Third Day of April, 2001

*Attest:*

NICHOLAS P. GODICI

*Attesting Officer*     *Acting Director of the United States Patent and Trademark Office*